(12) United States Patent
Kawahara et al.

(10) Patent No.: US 7,601,151 B2
(45) Date of Patent: Oct. 13, 2009

(54) ENDOSCOPIC HIGH-FREQUENCY TREATMENT TOOL

(75) Inventors: Yoshiro Kawahara, Okayama (JP); Hiroaki Shibata, Saitama (JP)

(73) Assignee: Hoya Corporation, Tokyo (JP)

( * ) Notice: Subject to any disclaimer, the term of this patent is extended or adjusted under 35 U.S.C. 154(b) by 451 days.

(21) Appl. No.: 11/344,079

(22) Filed: Feb. 1, 2006

(65) Prior Publication Data
US 2006/0173451 A1   Aug. 3, 2006

(30) Foreign Application Priority Data
Feb. 2, 2005   (JP) .............................. 2005-025799

(51) Int. Cl.
*A61B 18/14* (2006.01)
(52) U.S. Cl. .......................................... 606/45; 606/46
(58) Field of Classification Search ............. 606/45–47
See application file for complete search history.

(56) References Cited

U.S. PATENT DOCUMENTS

| | | | | |
|---|---|---|---|---|
| 4,325,374 | A | * | 4/1982 | Komiya ........................ 606/47 |
| 4,887,593 | A | | 12/1989 | Wiley et al. |
| 5,075,062 | A | * | 12/1991 | Karpiel ..................... 264/171.2 |
| 5,643,294 | A | * | 7/1997 | Tovey et al. ................. 606/148 |
| 5,984,920 | A | * | 11/1999 | Steinbach .................... 606/47 |
| 6,190,384 | B1 | | 2/2001 | Ouchi |
| 6,299,612 | B1 | | 10/2001 | Ouchi |
| 6,331,166 | B1 | * | 12/2001 | Burbank et al. ............... 606/45 |
| 6,514,248 | B1 | * | 2/2003 | Eggers et al. ................. 606/41 |
| 6,712,817 | B1 | * | 3/2004 | Goto et al. .................... 606/47 |
| 2002/0072688 | A1 | | 6/2002 | Burbank et al. |
| 2004/0092953 | A1 | | 5/2004 | Salameh et al. |
| 2005/0049454 | A1 | | 3/2005 | Ouchi |
| 2005/0261675 | A1 | | 11/2005 | Shibata |

FOREIGN PATENT DOCUMENTS

JP    57-000811    1/1982
JP    9-164148    6/1997

OTHER PUBLICATIONS

U.S. Appl. No. 11/344,078 to Shibata, which was filed on Feb. 1, 2006.
English Language Abstract of JP 9-164148.

* cited by examiner

*Primary Examiner*—Lee S Cohen
(74) *Attorney, Agent, or Firm*—Greenblum & Bernstein, P.L.C.

(57) ABSTRACT

An endoscopic high-frequency treatment tool includes an insulating flexible sheath; a conductive stranded wire made of metal; and a cover sheath which is fitted on a portion of the conductive stranded wire in the vicinity of a end thereof. The conductive stranded wire is inserted into the insulating flexible sheath so as to be rotatable about an axis of the conductive stranded wire from a proximal end side thereof, and a part of wire strands of the conductive stranded wire is extended outwards from a portion of the insulating flexible sheath in the vicinity of a end thereof to be used as a high-frequency cutting electrode.

2 Claims, 2 Drawing Sheets

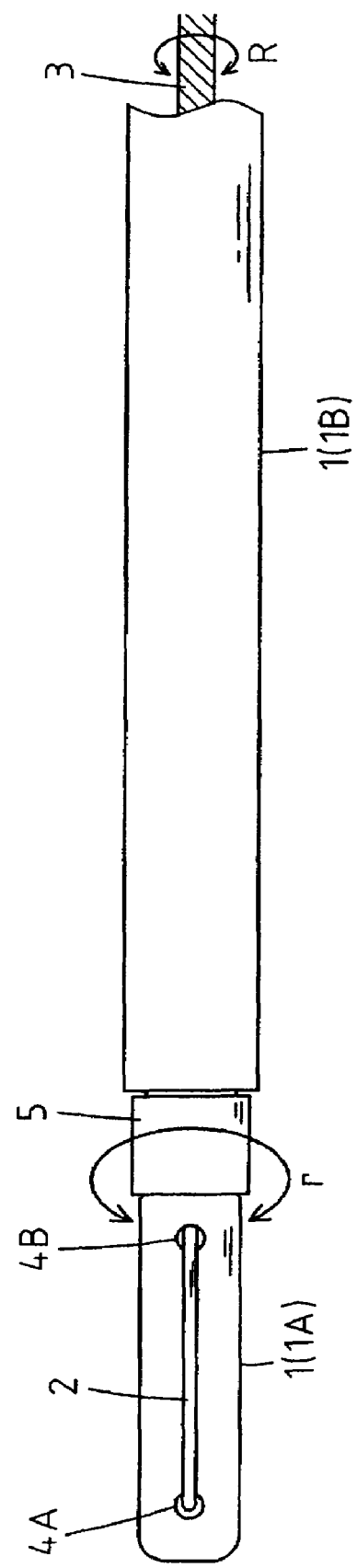

ENDOSCOPIC HIGH-FREQUENCY TREATMENT TOOL

BACKGROUND OF THE INVENTION

1. Field of the Invention

The present invention relates to an endoscopic high-frequency treatment tool which is inserted into a treatment tool insertion channel of an endoscope.

2. Description of the Related Art

A typical endoscopic high-frequency treatment tool is constructed and arranged so that a conductive wire is inserted into an insulating flexible sheath, which is inserted into a treatment tool insertion channel of an endoscope, and so that a high-frequency cutting electrode exposed at the outer surface of the flexible sheath in the vicinity of the end thereof and the conductive wire are connected together in the flexible sheath.

However, an operation connecting the conductive wire that is inserted into the flexible sheath and the high-frequency cutting electrode to each other needs to be performed with a high degree of precision. If the connection between the conductive wire and the high-frequency cutting electrode is even a little poor, there is a possibility of the high-frequency cutting electrode falling into the body of a patient.

To prevent this problem from occurring, an endoscopic high-frequency treatment tool in which a stranded wire made of metal is used as a conductive wire and in which a part of the strands having the conductive wire is extended from the conductive wire to be used as a high-frequency cutting electrode is known in the art. This type of endoscopic high-frequency treatment tool is disclosed in Japanese patent gazette No. 57-811.

However, if a part of the strands of the conductive wire is extended from the conductive wire to be used as a high-frequency cutting electrode, the end of the conductive wire which corresponds to the base (root) of the high-frequency cutting electrode may become frayed and thus expand radially to thereby cause a malfunction. This problem tends to occur especially in the case where the conductive wire is operated to rotate about its axis in the flexible sheath.

FIG. 7 of the aforementioned Japanese patent gazette shows an embodiment of an endoscopic high-frequency treatment tool in which a high-frequency cutting electrode formed by a part of the strands of a conductive wire is looped to extend backward and then joined at the end of the high-frequency cutting electrode to the end surface of the conductive wire. However, such a structure cannot securely prevent the conductive wire that is made of strands from becoming frayed when the conductive wire is repeatedly rotated about its axis. Moreover, if the end of the high-frequency cutting electrode is soldered to the end surface of the conductive wire, the subsequent flux-residue cleaning operation becomes extremely troublesome. Furthermore, if the end of the high-frequency cutting electrode is brazed to the end surface of the conductive wire, the application of heat during brazing weakens the base of the high-frequency cutting electrode, and therefore may cause the high-frequency cutting electrode to be damaged during use.

SUMMARY OF THE INVENTION

The present invention provides an endoscopic high-frequency treatment tool wherein a stranded wire is used as a conductive wire and wherein a part of the strands having the stranded wire is extended from the stranded wire to be used as a high-frequency cutting electrode, and wherein the end of the conductive wire is prevented from becoming frayed and expanding radially even if the conductive wire is repeatedly rotated.

According to an aspect of the present invention, an endoscopic high-frequency treatment tool is provided, including an insulating flexible sheath; a conductive stranded wire made of metal; and a cover sheath which is fitted on a portion of the conductive stranded wire in the vicinity of a end thereof, wherein the conductive stranded wire is inserted into the insulating flexible sheath so as to be rotatable about an axis of the conductive stranded wire from a proximal end side thereof, and a part of wire strands of the conductive stranded wire is extended outwards from a portion of the insulating flexible sheath in the vicinity of a end thereof to be used as a high-frequency cutting electrode.

It is desirable for the high-frequency cutting electrode to be positioned so that an outer surface thereof is exposed at a side surface of the insulating flexible sheath in the vicinity of the end thereof. The insulating flexible sheath includes a distal portion and a proximal portion which are separated from each other at a separation position behind the high-frequency cutting electrode on a proximal side thereof in the vicinity of the end of the insulating flexible sheath. The distal portion and the proximal portion are connected to each other at the separation position to be freely rotatable relative to each other about a common axis which is also common with an axis of the insulating flexible sheath, so that the distal portion rotates about the common axis by rotating the conductive stranded wire from a proximal end of the proximal portion.

It is desirable for the distal portion to include two holes which are provided apart from each other in a direction substantially parallel to the axis of the distal portion, the outer surface of the high-frequency cutting electrode being exposed at the side surface of the insulating flexible sheath via the two holes to extend in the direction substantially parallel to the axis of the distal portion.

It is desirable for the end of the conductive stranded wire to be drawn into the distal portion through one of the two through-holes and to be wound tightly around the cover sheath to fix the cover sheath to the conductive stranded wire.

It is desirable for the cover sheath to be made of a heat-shrinkable material.

In an embodiment, an endoscopic high-frequency treatment tool is provided, including an insulating flexible sheath including a proximal portion and a distal portion which is connected to the proximal portion to be freely rotatable on an axis of the distal portion relative to the proximal portion; a conductive stranded wire inserted into the insulating flexible sheath so that a part of wire strands of the conductive stranded wire is exposed to the outside of the distal portion to serve as a high-frequency cutting electrode, wherein rotating the conductive stranded wire on an axis thereof relative to the insulating flexible sheath therein causes the distal portion to rotate about the axis thereof relative to the proximal portion; and a cover sheath which is fitted on a portion of the conductive stranded wire in the vicinity of a end thereof to prevent the conductive stranded wire from expanding radially.

According to the present invention, the arrangement wherein a sheath for preventing the conductive stranded wire from expanding radially is fitted on a portion of the conductive stranded wire in the vicinity of the end thereof prevents the end of the conductive stranded wire from becoming frayed and expanding radially even if the conductive stranded wire is repeatedly rotated about its axis. Moreover, since the end of the high-frequency cutting electrode is joined to the end surface of the conductive stranded wire by neither soldering nor brazing, no flux-residue cleaning operation is required and the high-frequency cutting electrode is not weakened via application of heat, which makes it possible to reliably prevent the conductive stranded wire from becoming frayed.

The present disclosure relates to subject matter contained in Japanese Patent Application No. 2005-25799 (filed on Feb. 2, 2005) which is expressly incorporated herein by reference in its entirety.

BRIEF DESCRIPTION OF THE DRAWINGS

The present invention will be discussed below in detail with reference to the accompanying drawings, in which:

FIG. 2 is a plan view of the end portion of the endoscopic high-frequency knife shown in FIG. 1.

DESCRIPTION OF THE PREFERRED EMBODIMENT

Figure 1:
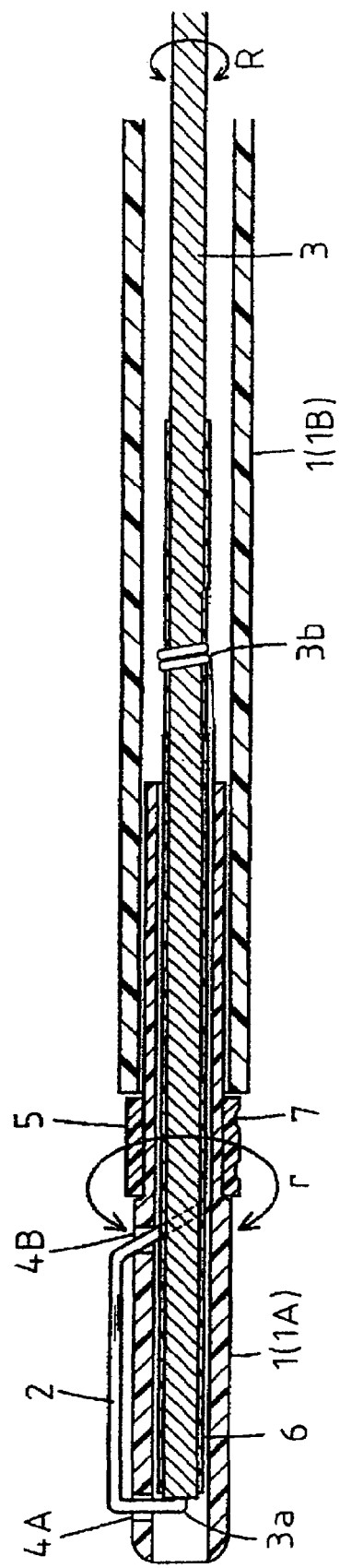
FIG. 1 is an axial sectional view of a end portion of an embodiment of an endoscopic high-frequency knife according to the present invention.

FIGS. 1 and 2 show an end portion (distal end portion) of an embodiment of an endoscopic high-frequency knife according to the present invention. The endoscopic high-frequency knife is provided with an insulating flexible sheath 1, a high-frequency cutting electrode 2 and a conductive wire (conductive stranded wire) 3. The insulating flexible sheath 1 is a flexible tube made of resin such as polytetrafluoroethylene (PTFE). The high-frequency cutting electrode 2 is installed in the endoscopic high-frequency knife so that an outer surface of the high-frequency cutting electrode 2 is exposed at a side surface of the flexible sheath 1 in the vicinity of the end thereof. The conductive wire 3 which is inserted into the flexible sheath 1 is joined to the high-frequency cutting electrode 2 to establish electrical connection therewith.

The flexible sheath 1 is separated into two portions: a distal portion 1A and a proximal portion 1B in the vicinity of the distal end of the flexible sheath 1 a little away from the high-frequency cutting electrode 2 toward the proximal end side of the flexible sheath 1 (e.g., at a position 3 to 10 centimeters away from the end of the flexible sheath 1).

Specifically, the proximal portion 1B is formed to be, e.g., approximately 1.5 to 3 millimeters in diameter and approximately 1 to 2 meters in length, and the distal portion 1A is formed to have an outer diameter that allows the distal portion 1A to be loosely fitted into the distal end of the proximal portion 1B by a length of approximately 1 to 2 centimeters and to be capable of rotating freely on the axis of the distal portion 1A relative to the proximal portion 1B.

In the present embodiment, the conductive wire 3 is a stranded wire consisting of a plurality of wire strands (conductive wire strands). The plurality of wire strands consists of a straight core strand and the remaining wire strands (e.g., five or six wire strands) which surrounds the straight core strand. The end of the core strand is extended from the end of the stranded wire to be partly formed as the high-frequency cutting electrode 2. One or more wire strands of the conductive wire 3 other than the core strand of the conductive wire 3 can be extended from the end of the stranded wire to be formed as the high-frequency cutting electrode 2.

The distal portion 1A is provided, on the periphery thereof in the vicinity of the opposite ends of the distal portion 1A, respectively, with a pair of through-holes (radial holes) 4A and 4B, respectively, which are spaced from each other in the lengthwise direction (axial direction) of the distal portion 1A. An extended part 3a of the core strand of the conductive wire 3 is drawn out of the distal portion 1A through the through-hole 4A and bent backward (rightward as viewed in FIG. 1). Subsequently, the end of the backwardly bent portion of the extended part 3a is drawn back into the distal portion 1A through the through-hole 4B so that a portion of the extended part 3a which is exposed to the outside of the distal portion 1A between the pair of through-holes 4A and 4B serves as the high-frequency cutting electrode 2.

The end 3b of an extended part of the core strand that is drawn into the distal portion 1A through the through-hole 4B extends backward up into the proximal portion 1B and is wound around the conductive wire 3 in the proximal portion 1B in the vicinity of the end thereof. Due to this structure, the end of the conductive wire 3 is substantially fixed to the distal portion 1A.

A portion of the conductive wire 3 in the vicinity of the end thereof is sheathed with a sheath (cover sheath) 6 which prevents the conductive wire 3 from becoming frayed and expanding radially. In view of resistance to high-frequency and heat which are generated during an endoscopic high-frequency treatment, the sheath 6 is formed from a material such as a fluorocarbon resin, a polyimide resin, or a polyether-ether-keton (PEEK) resin.

Although it is sufficient for the aforementioned portion of the conductive wire 3 which is sheathed with the sheath 6 to extend by a length of approximately a few millimeters to a few centimeters from the end of the conductive wire 3, the same portion to be sheathed with the sheath 6 can extend by a greater length. In the present embodiment, the sheathed portion of the conductive stranded wire 3 that is sheathed with the sheath 6 extends approximately three to five centimeters.

The inner diameter of the sheath 6 is substantially identical to the outer diameter of the conductive wire 3 (slightly greater than the outer diameter of the conductive wire 3, to be exact, so that the sheath 6 can be firmly fitted on the conductive wire 3), and the wall thickness of the sheath 6 only needs to be within the range sufficient for the conductive wire 3 to be prevented from being frayed (e.g., the range from 0.15 to 0.25 millimeters).

The sheath 6 is fixed to the conductive wire 3 by winding the end 3b of the extended part of the core strand, which is drawn into the distal portion 1A through the through-hole 4B, tightly around the outer periphery of the sheath 6. If a heat-shrinkable sheath having an inner diameter greater than the outer diameter of the conductive wire to some extent is used as the sheath 6, the sheath 6 can be fixed on the conductive wire 3 by heat contraction force.

Since the sheath 6 of such a type which is firmly fitted on a portion of the conductive wire 3 in the vicinity of the end thereof, the end of the conductive wire 3 does not become frayed and thus does not expand radially even if the conductive wire 3 is repeatedly rotated about its axis. Moreover, since the end of the high-frequency cutting electrode is joined to the end surface of the conductive wire by neither soldering nor brazing, no flux-residue cleaning operation is required and the high-frequency cutting electrode is not weakened by an application of heat, which makes it possible to reliably prevent the conductive wire 3 from becoming frayed.

The endoscopic high-frequency knife is provided, on an outer peripheral surface of the distal portion 1A in close vicinity of the end of the proximal portion 1B, with a stopper tube 5 which is firmly fitted on the distal portion 1A, e.g., by being heat-shrunk thereon. The stopper tube 5 prevents the distal portion 1A from being further drawn into the proximal portion 1B when an external force which makes the distal portion 1A move in the axial direction thereof relative to the proximal portion 1B is exerted on the distal portion 1A. The conductive wire 3 together with the high-frequency cutting electrode 2 serves as a stopper which prevents the distal portion 1A from coming out of the proximal portion 1B.

The endoscopic high-frequency knife is provided with indicia (marks) 7 on the stopper tube 5 in a rearward axial direction extending from the distal portion 1A on the circumferentially opposite side of the distal portion 1A from the high-frequency cutting electrode 2.

A manual operation portion (not shown) is coupled to the proximal end of the proximal portion 1B. Manually rotating the conductive wire 3 on the axis thereof in directions shown by double-headed arrows R in FIGS. 1 and 2 causes the distal portion 1A to rotate on the axis thereof relative to the proximal portion 1B in directions shown by double-headed arrows r in FIGS. 1 and 2, thus causing the high-frequency cutting electrode 2 to rotate about the axis of the sheath 1. Electric current can be passed through the high-frequency cutting electrode 2 via the high-frequency cutting electrode 2 by connecting a line cord of a high-frequency power supply (not shown) to the manual operation portion.

Due to such a structure, in the case where one makes numerous consecutive incisions in, e.g., a swelled resection part of a mucosa with an endoscopic high-frequency knife, incisions can be easily made in the swelled resection part in a short time with the above illustrated embodiment of the endoscopic high-frequency knife. This is because one can reorient the high-frequency cutting electrode 2 to change the incisional position for the subsequent incising operation instantly by changing the orientation of the high-frequency cutting electrode 2 by approximately 180 degrees each time an incision has been made in the swelled resection part by swinging the flexible sheath 1 with the high-frequency cutting electrode 2 in an energized state.

The present invention is not limited solely to the particular embodiment described above. For instance, the present invention can be applied to various types of endoscopic high-frequency treatment tools.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscopic high-frequency treatment tool comprising:
    an insulating flexible sheath;
    a conductive stranded wire made of metal; and
    a cover sheath which is fitted on a portion of said conductive stranded wire in the vicinity of an end thereof,
    said conductive stranded wire being inserted into said insulating flexible sheath so as to be rotatable about an axis of said conductive stranded wire from a proximal end side thereof,
    a part of wire strands of said conductive stranded wire extending outwardly from a portion of said insulating flexible sheath in the vicinity of an end thereof to be used as a high-frequency cutting electrode,
    said high-frequency cutting electrode being positioned so that an outer surface thereof is exposed at a side surface of said insulating flexible sheath in the vicinity of said end thereof,
    said insulating flexible sheath including a distal portion and a proximal portion which are separated from each other at a separation position behind said high-frequency cutting electrode on a proximal side thereof in the vicinity of said end of said insulating flexible sheath,
    said distal portion and said proximal portion being connected to each other at said separation position to be freely rotatable relative to each other about a common axis which is also common with an axis of said insulating flexible sheath, so that said distal portion rotates about said common axis by rotating said conductive stranded wire from a proximal end of said proximal portion,
    said distal portion including two holes which are provided apart from each other in a direction substantially parallel to said axis of said distal portion, said outer surface of said high-frequency cutting electrode being exposed at said side surface of said insulating flexible sheath via said two holes to extend in said direction substantially parallel to said axis of said distal portion, and
    said end of said conductive stranded wire being drawn into said distal portion through one of said two through-holes and is wound tightly around said cover sheath to fix said cover sheath to said conductive stranded wire.

2. The endoscopic high-frequency treatment tool according to claim 1, wherein said cover sheath is made of a heat-shrinkable material.

* * * * *